United States Patent [19]

Unangst

[11] Patent Number: 4,596,814
[45] Date of Patent: Jun. 24, 1986

[54] TETRAZOLYL- AND CARBOXAMIDOTETRAZOLYL-SUBSTITUTED 4H-FURO[3,2-B] INDOLES AND ANTI-ALLERGIC USE THEREOF

[75] Inventor: Paul C. Unangst, Ann Arbor, Mich.

[73] Assignee: Warner-Lambert Company, Morris Plains, N.J.

[21] Appl. No.: 679,337

[22] Filed: Dec. 7, 1984

Related U.S. Application Data

[63] Continuation-in-part of Ser. No. 456,121, Jan. 10, 1983, Pat. No. 4,503,236, which is a continuation-in-part of Ser. No. 369,448, Apr. 19, 1982, abandoned.

[51] Int. Cl.[4] .................. C07D 491/048; A61K 31/41
[52] U.S. Cl. .................................... 514/382; 548/251; 548/253; 548/453
[58] Field of Search ................ 548/251, 253; 424/269; 514/382

[56] References Cited

U.S. PATENT DOCUMENTS 3,839,339 10/1974 Ellis et al. ........................... 548/253
4,028,383 6/1977 Brown et al. .................. 260/326.29
4,288,596 9/1981 Kameyama ......................... 546/198

FOREIGN PATENT DOCUMENTS 2004885 9/1977 United Kingdom .
0092380 10/1983 United Kingdom ................ 548/251

OTHER PUBLICATIONS

Yoshina et al., Chem. Abst. 82, 1975, Abst. 170867y of Japan Kokai 74:125, 396, Nov. 30, 1974.

Primary Examiner—Glennon H. Hollrah
Assistant Examiner—D. B. Springer
Attorney, Agent, or Firm—Jerry F. Janssen

[57] ABSTRACT

Novel tetrazolyl- and carboxamidotetrazolyl-substituted 4H-furo[3,2-b] indoles are useful for treating allergies or for treating or ameliorating postmyocardial infarct tissue damage. Also disclosed are methods for preparing said indoles, pharmaceutical compositions containing said indoles and methods for using said pharmaceutical compositions.

13 Claims, No Drawings

TETRAZOLYL- AND CARBOXAMIDOTETRAZOLYL-SUBSTITUTED 4H-FURO[3,2-B] INDOLES AND ANTI-ALLERGIC USE THEREOF

CROSS-REFERENCE TO RELATED APPLICATION

This application is a continuation-in-part of application Ser. No. 456,121 filed Jan. 10, 1983, now U.S. Pat. No. 4,503,236 issued Mar. 5, 1985, which in turn is a continuation-in-part of application Ser. No. 369,448 filed Apr. 19, 1982, now abandoned.

BACKGROUND OF THE INVENTION

U.S. Pat. No. 4,288,596 discloses certain substituted furo[3,2-b]indoles which are reported to have anti-inflammatory and analgesic effects.

SUMMARY OF THE INVENTION

The invention sought to be patented in its generic chemical compound aspect is a compound having the structural formula I $R_3$ is

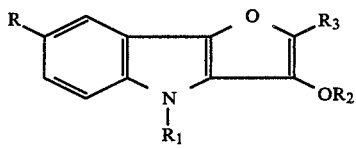

wherein R is H, alkyl of from one to six carbon atoms, alkoxy of from one to six carbon atoms, halogen or nitro; $R_1$ is alkyl of from one to six carbon atoms, phenyl or benzyl; $R_2$ is alkyl of from one to six carbon atoms; $R_3$ is

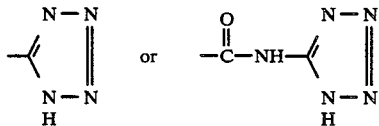

and the pharmaceutically acceptable salts thereof.

The invention sought to be patented in a first specific chemical compound aspect is the compound having the name 3,7-dimethoxy-4-phenyl-N-(1H-tetrazol-5-yl)4H-furo[3,2-b]indole-2-carboxamide, and the pharmaceutically acceptable salts thereof.

The invention sought to be patented in a second specific chemical compound aspect is the compound having the name 3-ethoxy-4-phenyl-N-(1H-tetrazol-5-yl)-4H-furo[3,2-b]indole-2-carboxamide, and the pharmaceutically acceptable salts thereof.

The invention sought to be patented in a third specific chemical compound aspect is the compound having the name 3-methoxy-4-phenyl-2-(1H-tetrazol-5-yl)-4H-furo[3,2-b]indole, and the pharmaceutically acceptable salts thereof.

The invention sought to be patented in a fourth specific chemical compound aspect is the compound having the name 3-ethoxy-4-phenyl-2-(1H-tetrazol-5-yl)-4H-furo[3,2-b]indole, and the pharmaceutically acceptable salts thereof.

The invention sought to be patented in an fifth specific chemical compound aspect is the compound having the name 3-methoxy-4-phenyl-N-(1H-tetrazol-5-yl)-4H-furo[3,2-b]indole-2-carboxamide, and the pharmaceutically acceptable salts thereof.

The invention sought to be patented in a sixth specific chemical compound aspect is the compound having the name 3-methoxy-4-methyl-N-(1H-tetrazol-5-yl)-4H-furo[3,2-b]indole-2-carboxamide, and the pharmaceutically acceptable salts thereof.

The invention sought to be patented in an seventh specific chemical compound aspect is the compound having the name 3-ethoxy-7-methoxy-4-phenyl -N-(1H-tetrazol-5yl)-4H-furo[3,2-b]indole-2-carboxamide, and the pharmaceutically acceptable salts thereof.

The invention sought to be patented in a eighth specific chemical compound aspect is the compound having the name 3-methoxy-4-methyl-2-(1H-tetrazol-yl)-4H-furo[3,2-b]indole, and the pharmaceutically acceptable salts thereof.

The invention sought to be patented in a ninth specific chemical compound aspect is the compound having the name 3,7-dimethoxy-4-phenyl-2-(1H-tetrazol-5-yl)-4H-furo[3,2-b]indole, and the pharmaceutically acceptable salts thereof.

The invention sought to be patented in its generic chemical process aspect is a process for preparing a compound having structural formula I which comprises the steps of:

(a) alkylating a compound having the structural formula IV

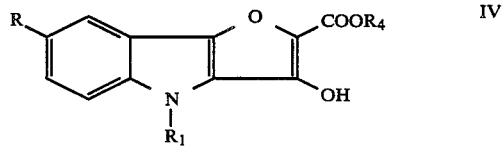

to produce a compound having the structural formula V

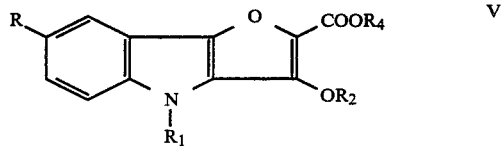

wherein R, $R_1$, and $R_2$ are as defined above and $R_4$ may be any convenient alkyl group, (b) hydrolyzing the ester function of Compound V to produce the corresponding carboxylic acid if desired;

(c) converting the carboxylic acid or ester to the corresponding 1H-tetrazol-5-yl compound or N-(1H-tetrazol-5-yl)carboxamide if desired; and (d) optionally converting the compound having structural formula I to a pharmaceutically acceptable salt.

The invention sought to be patented in its generic pharmaceutical composition aspect is a composition consisting essentially of a compound having structural formula I in combination with a pharmaceutically acceptable carrier.

The invention sought to be patented in one pharmaceutical method aspect is a method for treating allergies in a mammal in need of such treatment which comprises administering an effective amount of the above defined pharmaceutical composition to said mammal.

The invention ought to be patented in a second pharmaceutical method aspect is a method for treating postmyocardial infarct tissue damage in a mammal in need of such treatment which comprises administering a neutrophil-inhibiting effective amount of a compound as defined above to said mammal.

DESCRIPTION OF THE PREFERRED EMBODIMENTS

The compounds of the invention having structural formula I wherein $R_3$ is COOH are readily prepared by the following reaction sequence.

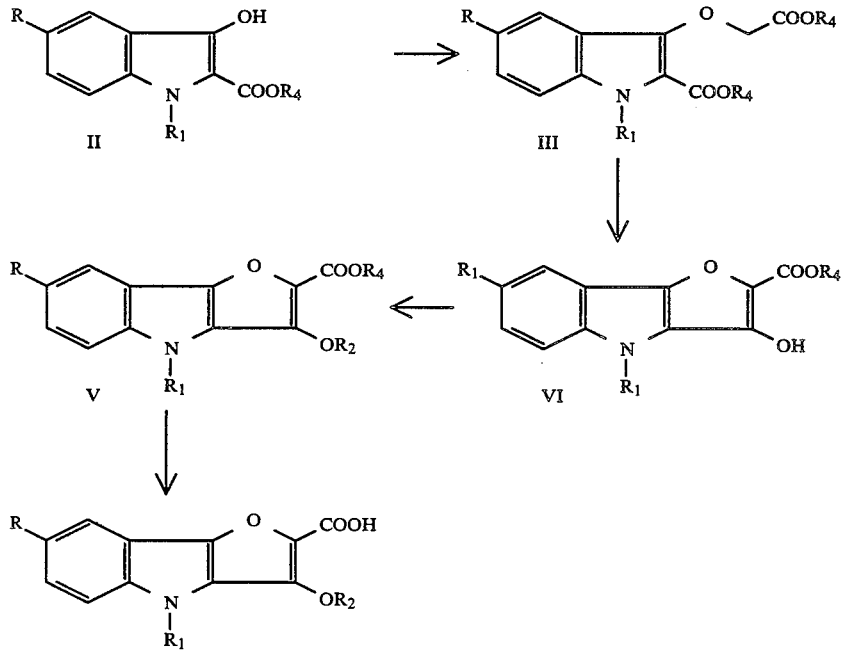

The starting materials having structural formula II are readily prepared by known procedures [see *Berichte*, 55, 1597 (1922) which describes Compound II wherein R=H]. Compound II is converted to Compound III by treatment with an ester of a haloacetic acid such as methyl bromoacetate in the presence of anhydrous potassium carbonate in a convenient solvent such as acetone. The two $R_4$ groups in structural formula III represent any convenient alkyl groups such as methyl or ethyl and they may be the same or different.

Compound III may next be treated with a strong base such as potassium-t-butoxide in a convenient solvent such as tetrahydrofuran to produce the compound having structural formula IV.

The hydroxyl group of Compound IV may next be alkylated in a conventional manner to produce Compound V. A convenient alkylating procedure utilizes a dialkylsulfate such as dimethylsulfate in the presence of a base such as potassium carbonate in a convenient solvent such as acetone.

The ester function of Compound V may then by hydrolyzed for example in an alcoholic basic medium such as methanolic sodium hydroxide to produce the compounds of formula I wherein $R_3$ is COOH.

The compounds of the invention wherein $R_3$ is

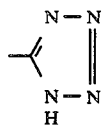

may be prepared from the corresponding acids or esters by methods familiar to those skilled in the art. For example, the properly substituted carboxylic acid may be converted to the corresponding acid halide such as the chloride by treatment with thionyl chloride or oxalyl chloride and converted to the acid amide by treatment with ammonia. The amide is dehydrated by treatment with, for example, p-toluenesulfonyl chloride and pyridine in dimethylformamide thereby producing the corresponding nitrile, which when treated with sodium azide and aluminum chloride, for example, will yield the corresponding tetrazole. The above-described amides may also be prepared directly from the corresponding esters by treatment with, for example, lithium amide in liquid ammonia by methods familiar to those skilled in the art.

Other methods and reagents for converting carboxylic acids or esters into the corresponding tetrazoles will be familiar to those skilled in the art.

The compounds of the invention wherein $R_3$ is

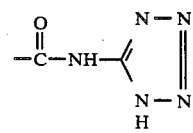

may be prepared from the corresponding acid halide, such as the above-described acid chloride, by treatment with 5-aminotetrazole. Alternatively, the properly substituted carboxylic acid may be directly coupled with 5-aminotetrazole; by use of such agents as N-ethoxycarbonyl-2-ethoxy-1,2-dihydroquinolone (EEDQ), dicyclohexylcarbodiimide (DCC) or 1,1'-carbonyldiimidazole and the like.

The compounds of the invention having structural formula I wherein $R_3$ is $$-\!\!\!\stackrel{\displaystyle N-N}{\underset{\displaystyle N-N}{\Bigg\langle}}\!\!\!\underset{H}{\Bigg|} \quad \text{or} \quad -\overset{O}{\underset{\Vert}{C}}-NH-\!\!\!\stackrel{\displaystyle N-N}{\underset{\displaystyle N-N}{\Bigg\langle}}\!\!\!\underset{H}{\Bigg|}$$

are acidic in nature and form pharmaceutically acceptable salts with both organic and inorganic bases such as alkyl amines, especially tertiary alkyl amines such as triethylamine, hydroxylated alkyl amines such as tris(-hydroxymethyl)aminomethane, cycloaliphatic amines such as piperidine, alkylene diamines such as 1,2-ethanediamine, and basic amino acids such as L-(+) arginine, the alkali metal and alkaline earth hydroxides, and the alkali metal carbonates and bicarbonates, such as lithium, sodium, potassium, and calcium hydroxide, and the carbonates and bicarbonates of lithium, sodium, and potassium. The salts are prepared by reacting the tetrazole or the carboxamidotetrazole with the desired base in the conventional manner. The tetrazoles and the carboxamidotetrazoles differ from their respective salts somewhat in certain physical properties such as solubility in polar solvents, but the salts are otherwise equivalent to their respective acids for purposes of the invention.

The compounds of the invention display antiallergic properties when tested by the following procedure [modification of Shultz-Dale procedure, *Agents and Actions*, 8, 171 (1978)]: Guinea pigs, after one week environmental stabilization, are immunized IP with 1 mg crude ovalbumin (OA) in 1 ml saline with 50% complete Freund's Adjuvant (CFA). Twenty-one days later animals are killed by a blow to the head. Trachea and lungs are removed and placed in Tyrode's solution, pH 7.4, aerated with 5% $CO_2$ in $O_2$.

Trachea: Connective and vascular tissue are removed and a wooden stick is inserted in the lumen. One end of the trachea is fixed with a pin. The stick is held against a surgical blade and rotated in a helical manner. Spirals formed are cut into two lengths, each containing two or more bands of transverse strips of tracheal muscle. The tissue is attached to transducers and maintained at 5 g tension. Sensitivity of the preamplifier is 2.0 mv/cm and of the amplifier, 0.02 mv/cm, with calibration of 20 mg force displacement per mm. After 45 minutes equilibration, the tissue is challenged with antigen.

Lung: The heart and lung are removed as a unit and the lung is perfused with buffer by the spontaneously beating heart for several minutes. Distal strips of lung from the diaphragmatic lobe approximately 0.3 cm wide and 3 cm long are removed and attached to transducers. Preload is 0.3 g of tension with sensitivity at 0.02 mv/cm on the amplifier and 0.5 mv/cm on the preamp and calibration of 1 mm=5 mg force displacement.

Test Design for Evaluation of Drugs: All tissues are challenged repetitively with the same concentration of antigen. After each concentration, the tissue is washed and allowed to stabilize. The original baseline tension is reestablished before the next challenge. Control contractions in lung must develop a minimum of 10 mg and in trachea, a minimum of 40 mg tension above baseline. When the contractions are reproducible, drug is introduced. Drug effects of baseline are monitored. Ten minutes later, after readjustment to baseline tension as indicated by consecutive reading one minute apart, tissue is again challenged with antigen. The concentration is monitored for at least 15 minutes and the tissue is washed free of antigen and drug. If the drug did not exhibit the Schultz-Dale reaction, the experiment is complete. Tissues are not used again. If inhibition takes place, a final antigen challenge is repeated to establish that the tissue is reactive to antigen.

Utilizing the above test procedure, the following results were obtained for representative compounds of the invention.

TABLE 1

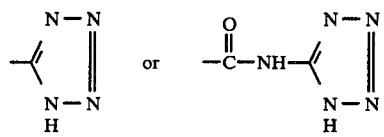

| R | $R_1$ | $R_2$ | $R_3$ | % Inhibition $3 \times 10^{-5}$ M |
|---|---|---|---|---|
| H | $CH_3$ | $CH_3$ | $-\overset{O}{\underset{\Vert}{C}}-NH-\!\!\stackrel{N-N}{\underset{\underset{H}{N-N}}{\Bigg\langle}}$ | 38 |
| H | $C_6H_5$ | $CH_3$ | " | 100 |
| $CH_3O$ | $C_6H_5$ | $CH_3$ | " | 100 |
| $CH_3O$ | $C_6H_5$ | $C_2H_5$ | " | 100 |
| H | $C_6H_5$ | $C_2H_5$ | " | 100 |
| H | $CH_3$ | $CH_3$ | $-\!\!\stackrel{N-N}{\underset{\underset{H}{N-N}}{\Bigg\langle}}$ | 26 |
| $CH_3O$ | $C_6H_5$ | $CH_3$ | " | 100 |
| H | $C_6H_5$ | $C_2H_5$ | " | 100 |

The compounds of the present invention have been found to also display the property of inhibiting the action of polymorphonuclear leukocytes (neutrophils).

Lautsch, *Texas Rep. Biol. Med.*, 39, 371 (1979) has demonstrated that in cases of myocardial infarction, there is an accumulation of polymorphonuclear leukocytes in the damaged myocardial tissue. Romson et al, *Circulation*, 67, 1016 (1983) state that stimulated neutrophils release highly active and cytotoxic activated oxygen species such as the superoxide anion, hydroxyl radical, hydrogen peroxide, and singlet oxygen. These activated oxygen radicals degrade extracellular macromolecules, attack membrane phospholipids, and thus promote cell injury. In addition, activated neutorophils release lysosomal enzymes capable of proteolytic disruption and liquefaction of viable as well as irreversibly damaged tissue. Finally, stimulated neutrophils trigger membrane phospholipids to release arachidonic acid, which is converted by specific lipoxygenases to potent chemotactic hydroxy-eicosatetraenoic acids (HETEs). These chemoattractant substances promote the further recruitment of neutrophils onto the acute inflammatory response at the site of the tissue injury.

The compounds of the present invention inhibit the action of activated neutrophils and are thus useful in the amelioration and treatment of postmyocardial infarct tissue damage. The neutrophil inhibitory properties of the compounds of this invention were tested by means of an assay which determined the percent inhibition of the release of myeloperoxidase, lysozyme, beta-glucuronidase, superoxide anion, and hydrogen peroxide by neutrophils. The details of the procotol of this assay appear in Wright, et al, *Infection and Immunity,* 32, 731 (1981). The results of the tests appear in Table 2.

suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with

TABLE 2

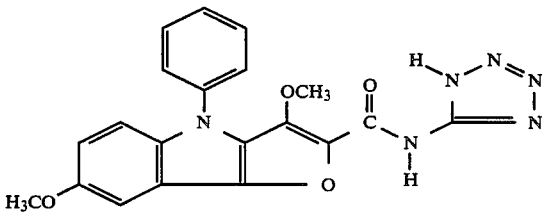

| Dose (μm/liter) | Myelo-peroxidase | Percent of Control | | Superoxide Anion | Hydrogen Peroxide |
| --- | --- | --- | --- | --- | --- |
| | | B—Glucuronidase | Lysosome | | |
| 1.0 | 96.8 ± 18.5 | 91.2 ± 15.7 | 96.0 ± 1.3 | 96.0 ± 5.8 | 77.7 ± 2.5 |
| 3.3 | 75.4 ± 29.8 | 67.1 ± 0.1 | 98.7 ± 6.8 | 98.7 ± 4.0 | 59.5 ± 2.8 |
| 10.0 | 40.4 ± 19.8 | 53.2 ± 9.8 | 56.4 ± 1.3 | 56.4 ± 0.7 | 34.3 ± 1.5 |
| 33.0 | 30.2 ± 17.4 | 43.0 ± 27.0 | 39.8 ± 4.1 | 39.8 ± 0.6 | 11.8 ± 4.3 |
| 100.0 | 43.7 ± 30.9 | 38.2 ± 19.3 | 13.6 ± 13.6 | 13.6 ± 4.1 | 20.1 ± 6.2 |
| IC$_{50}$ Value | 18.0 | 21.5 | 17.4 | 19.8 | 5.3 |

The compounds of the invention can exist in unsolvated as well as solvated forms, including hydrated forms. In general, the solvated forms, with pharmaceutically acceptable solvents such as water, ethanol, and the like are equivalent to the unsolvated forms for purposes of the invention.

The alkyl groups and alkoxy groups contemplated by the invention comprise both straight and branched carbon chains of from one to about six carbon atoms. Representative of such groups are methyl, ethyl, isopropyl, pentyl, 3-methylpentyl, methoxy, ethoxy, i-propoxy, and the like.

Some of the compounds of the invention may comprise an asymmetric carbon atom. The pure D isomer, pure L isomer, as well as mixtures thereof are contemplated by the invention. Asymmetric carbon atoms may be present in a substituent such as an alkyl group. All such isomers as well as mixtures thereof are intended to be included in the invention.

The compounds of the invention can be prepared and administered in a wide variety of oral and parenteral dosage forms. It will be obvious to those skilled in the art that the following dosage forms may comprise as the active component, either a compound of formula I, or a corresponding pharmaceutically acceptable salt of a compound of formula I, or a mixture of such compounds and/or salts.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as antiallergic agents, the compounds utilized in the pharmaceutical method of this invention are administered at the initial dosage of about 0.1 mg to about 100 mg per kilogram daily. A daily dose range of about 0.5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventor's preferred methods for preparing the compounds of the invention.

EXAMPLE 1

5-Methoxy-3-(2-methoxy-2-oxoethoxy)-1-phenyl-1H-indole-2-carboxylic acid methyl ester A mixture of 59.5 g (0.20 mole) of 3-hydroxy-5-methoxy-1-phenyl-1H-indole-2-carboxylic acid methyl ester, 32.0 g (0.23 mole) of potassium carbonate (anhydrous), and 19 ml (34.7 g, 0.23 mole) of methyl bromoacetate in 800 ml acetone was stirred at reflux for 24 hours. The mixture was cooled, and the insoluble material was filtered and washed several times with fresh acetone. The combined filtrates were evaporated to yield the crude diester product as an oil which slowly crystallized. A sample recrystallized several times from methanol was analytically pure, mp 97°–100° C.

EXAMPLE 2

3-Hydroxy-7-methoxy-4-phenyl-4H-furo[3,2-b]indole-2-carboxylic acid methyl ester A suspension of 30 g (0.27 mole) of potassium tert-butoxide in 400 ml of tetrahydrofuran was stirred and cooled in ice while a solution of 67.0 g (0.18 mole) of 5-methoxy-3-(2-methoxy-2-oxoethoxy)-1-phenyl-1H-indole-2-carboxylic acid methyl ester was added over 45 minutes. The rate of addition was adjusted to maintain the temperature of the reaction mixture at <15° C. The mixture was allows to slowly warm to room temperature and was stirred for 16 hours. The mixture was again cooled in ice, treated with 25 ml of glacial acetic acid, and added to 2.75 kg ice/water. After stirring for several hours, the solid was filtered, stirred in 1.0 l fresh water, and refiltered. Recrystallization from N,N-dimethylformamide/water yielded the furoindole product as a yellow solid of mp 141°–144° C. (49.8 g, 74% yield). An additional recrystallization from 2-methoxyethanol/water yielded a sample of analytical purity, mp 141°–143° C.

EXAMPLE 3

3,7-Dimethoxy-4-phenyl-4H-furo[3,2-b]indole-2-carboxylic acid methyl ester

A mixture of 30 g (0.089 mole) of 3-hydroxy-7-methoxy-4-phenyl-4H-furo[3,2-b]indole-2-carboxylic acid methyl ester, 13.4 g (0.098 mole) of anhydrous potassium carbonate, and 9.0 ml (12.0 g, 0.095 mole) of dimethyl sulfate in 525 ml acetone was stirred at reflux for 42 hours. The mixture was cooled and the insoluble material was washed several times with fresh acetone. The combined filtrates were evaporated, and the residue was recrystallized from methanol/water to yield to methoxy ester product (25.0 g, 80% yield), mp 89°–92° C. Several additional recrystallizations yielded an analytically pure sample, mp 93°–95° C.

EXAMPLE 4

3,7-Dimethoxy-4-phenyl-4H-furo[3,2-b]indole-2-carboxylic acid

A suspension of 11.5 g (0.033 mole) of 3,7-dimethoxy-4-phenyl-4H-furo[3,2-b]indole-2-carboxylic acid methyl ester in 200 ml of 50% aqueous ethanol was treated with 25 ml of 10% aqueous sodium hydroxide solution. After stirring at reflux for 90 minutes, the reaction mixture was cooled and distributed between 750 ml of water and 250 ml of dichloromethane. The insoluble material (primarily the sodium salt of the product) was removed by filtration. The filtrate layers were separated, and the organic layer was discarded. The aqueous layer was washed several times with fresh dichloromethane, cooled in ice, and acidified with 4N hydrochloric acid. The precipitate crude product was filtered and washed with water. The original insoluble sodium salt was stirred for several hours in 400 ml of cold 1N hydrochloric acid, and the product acid was filtered, washed with water, and combined with the material obtained from acidification of the original aqueous layer. The crude yield of the furoindole acid was 9.4 g (85%) yield). A sample recrystallized from acetone/water was analytically pure, mp 148° C. (dec).

EXAMPLE 5

3,7-Dimethoxy-4-phenyl-N-(1H-tetrazol-5-yl)-4H-furo[3,2-b]indole-2-carboxamide

A mixture of 7.5 g (0.022 mole) of 3,7-dimethoxy-4-phenyl-4H-furo[3,2-b]indole-2-carboxylic acid and 7.5 g (0.046 mole) of 1,1'-carbonyldiimidazole in 50 ml of N,N-dimethylformamide was stirred and heated on the steam bath for 30 minutes. The mixture was cooled, 2.6 g (0.026 mole) of 5-aminotetrazole monohydrate was added, and heating was continued for an additional 30 minutes. The cooled reaction mixture was added to 350 g ice/water and acidified with 4N hydrochloric acid. The precipitated product was filtered, washed with water, and recrystallized from N,N-dimethylformamide/water (charcoal) to yield 6.0 g (61% yield) of the tetrazole amide product as a complex containing 0.5 mole of N,N-dimethylformamide. An additional recrystallization as above yielded an analytically pure sample of mp 231° C. (dec).

EXAMPLE 6

3-Ethoxy-7-methoxy-4-phenyl-4H-furo[3,2-b]indole-2-carboxylic acid methyl ester

Prepared by the procedure described in Example 3, except that diethyl sulfate was substituted for dimethyl sulfate. There was obtained 5.0 g (36% yield) of the ethoxy ester product from 12.9 g (0.038 mole) of 3-hydroxy-7-methoxy-4-phenyl-4H-furo[3,2-b]indole-2-carboxylic acid methyl ester. Several recrystallizations from aqueous methanol yielded the product as white needles in analytical purity, mp 119°–120.5° C.

EXAMPLE 7

3-(2-Methoxy-2-oxoethoxy)-1-phenyl-1H-indole-2-carboxylic acid methyl ester

Prepared by the procedure described in Example 1 from 120 g (0.45 mole) of 3-hydroxy-1-phenyl-1H-indole-2-carboxylic acid methyl ester. Recrystallization of the crude product from ethyl acetate/hexane yielded 102 g (67% yield) of the diester, mp 76°-80° C. An additional recrystallization yielded an analytically pure sample, mp 76°-77° C.

EXAMPLE 8

3-Hydroxy-4-phenyl-4H-furo[3,2-b]indole-2-carboxylic acid methyl ester

Prepared by the procedure described in Example 2 from 29.0 g (0.085 mole) of 3-(2-methoxy-2-oxoethoxy)-1-phenyl-1H-indole-2-carboxylic acid methyl ester. Recrystallization of the crude product from ethanol yielded 15.9 g (60% yield) of the enol ester in analytical purity, mp 152°-154° C.

EXAMPLE 9

3-Methoxy-4-phenyl-4H-furo[3,2-b]indole-2-carboxylic acid methyl ester

Prepared by the procedure described in Example 3 from 16.0 g (0.052 mole) of 3-hydroxy-4-phenyl-4H-furo[3,2-b]indole-2-carboxylic acid methyl ester. Recrystallization of the crude product from aqueous ethanol yielded 13.5 g (81% yield) of the methoxy ester in analytical purity, mp 131°-133° C.

EXAMPLE 10

3-Ethoxy-4-phenyl-4H-furo[3,2-b]indole-2-carboxylic acid methyl ester

A mixture of 24.3 g (0.079 mole) of 3-hydroxy-4-phenyl-4H-furo[3,2-b]indole-2-carboxylic acid methyl ester and 10.7 g (0.095 mole) of potassium tertbutoxide in 240 ml of dimethyl sulfoxide was stirred and treated over 45 minutes with 64.4 g (54.7 ml, 0.42 mole) of diethyl sulfate. After stirring for 24 hours, the mixture was added to 1.5 kg of ice/water. The clear liquid was decanted from the resulting gummy product. Recrystallization of the residual gum from aqueous ethanol yielded 18.8 g (71% yield) of analytically pure ethoxy ester, mp 82°-84° C.

EXAMPLE 11

3-Methoxy-4-phenyl-4H-furo[3,2-b]indole-2-carboxylic acid

A suspension of 13.5 g (0.042 mole) of 3-methoxy-4-phenyl-4H-furo[3,2-b]indole-2-carboxylic acid methyl ester in 75 ml of methanol was treated with 70.6 ml of 1.0 N aqueous sodium hydroxide. The mixture was stirred at reflux for 17 hours, then added to 1.4 l of water. The insoluble material was filtered, added to 1.0 l of water, and acidified with acetic acid while cooling in an ice bath. The crude acid product was recovered by filtration. The original filtrate from the reaction mixture and 1.4 l of water was also cooled in ice and acidified with acetic acid. The crude product obtained was filtered and combined with the earlier crop. The combined crude products were stirred in 400 ml of water, filtered, and recrystallized from methanol. There was obtained 5.8 g (45% yield) of analytically pure acid, mp 154°-155° C.

EXAMPLE 12

3-Methoxy-4-phenyl-N-(1H-tetrazol-5-yl)-4H-furo[3,2-b]indole-2-carboxamide

Prepared by the procedure described in Example 5 from 6.1 g (0.020 mole) of 3-methoxy-4-phenyl-4H-furo[3,2-b]indole-2-carboxylic acid. Recrystallization of the crude product from N,N-dimethylformamide/water yielded 4.4 g (59% yield) of analytically pure tetrazole amide, mp 270° C. (dec).

EXAMPLE 13

3-Methoxy-4-methyl-4H-furo[3,2-b]indole-2-carboxylic acid

Prepared by the procedure described in Example 4 from 35.8 g (0.13 mole) of 3-methoxy-4-methyl-4H-furo[3,2-b]indole-2-carboxylic acid ethyl ester. The crude acid product obtained was 23 g (72% yield). A sample recrystallized from N,N-dimethylformamide/water was analytically pure, mp 141° C. (dec).

EXAMPLE 14

3-Methoxy-4-methyl-N-(1H-tetrazol-5-yl)-4H-furo[3,2-b]indole-2-carboxamide

A mixture of 1.9 g (0.0078 mole) of 3-methoxy-4-methyl-4H-furo[3,2-b]indole-2-carboxylic acid and 1.4 g (0.0086 mole) of 1,1'-carbonyldiimidazole in 20 ml of N,N-dimethylformamide was stirred and heated on the steam bath for 20 minutes. The mixture was cooled, 0.85 g (0.0083 mole) of 5-aminotetrazole monohydrate was added, and heating was continued for an additional 20 minutes. Upon cooling, the tetrazole amide product precipitated, and the solid was filtered and washed with water. Recrystallization from N,N-dimethylformamide/water yielded 1.1 g (38% yield) of the product, mp 235° C. (dec). An additional recrystallization as above yielded an analytically pure sample (same mp) as a complex containing 1.0 mole of N,N-dimethylformamide.

EXAMPLE 15

3-Methoxy-4-methyl-4H-furo[3,2-b]indole-2-carboxylic acid ethyl ester

Prepared by the procedure described in Example 3 from 47 g (0.18 mole) of 3-hydroxy-4-methyl-4H-furo-[3,2-b]indole-2-carboxylic acid ethyl ester. Recrystallization of the crude product from aqueous ethanol yielded 42.2 g (85% yield) of the methoxy ester product, mp 90°-92° C. An additional recrystallization as above yielded an analytically pure sample, mp 93°-95° C.

EXAMPLE 16

3-Hydroxy-4-methyl-4H-furo[3,2-b]indole-2-carboxylic acid ethyl ester

A suspension of 10.8 g (0.096 mole) of potassium tert-butoxide in 200 ml of benzene was treated over 15 minutes with a solution of 22.4 g (0.074 mole) of 3-(2-ethoxy-2-oxoethoxy)-1-methyl-1H-indole-2-carboxylic acid ethyl ester in 100 ml of benzene. The mixture was then stirred at reflux under a nitrogen atmosphere for 18 hours. The solvent was removed under vacuum, and the residue was cooled in ice and treated with 300 ml of ice water and 200 ml of chloroform. After acidification with acetic acid, the layers were separated, and the aqueous layer was washed with additional chloroform. The combined organic layers were washed with water, 5% aqueous sodium bicarbonate (twice), and again with water. After drying over anhydrous sodium sulfate, the organic layer was evaporated, and the residue was recrystallized from aqueous methanol. There was obtained 8.2 g (43% yield) of the enol ester product, mp 116°-119° C. Several additional recrystallizations as

EXAMPLE 17

3-(2-Ethoxy-2-oxoethoxy)-1-methyl-1H-indole-2-carboxylic acid ethyl ester

Prepared by the procedure described in Example 1 from 3-hydroxy-1-methyl-1H-indole-2-carboxylic acid ethyl ester and ethyl bromoacetate. The crude oil product obtained after evaporation was used for further synthesis without additional purification.

EXAMPLE 18

3-Ethoxy-7-methoxy-4-phenyl-4H-furo[3,2-b]indole-2-carboxylic acid

Prepared by the procedure described in Example 4 from 4.9 g (0.013 mole) of 3-ethoxy-7-methoxy-4-phenyl-4H-furo[3,2-b]indole-2-carboxylic acid methyl ester. The crude acid product obtained was 4.0 g (85%) yield). A sample recrystallized from 2-methoxyethanol was analytically pure, mp 166°–167° C.

EXAMPLE 19

3-Ethoxy-7-methoxy-4-phenyl-N-(1H-tetrazol-5-yl)-4H-furo[3,2-b]indole-2-carboxamide Prepared by the procedure described in Example 5 from 3.0 g (0.085 mole) of 3-ethoxy-7-methoxy-4-phenyl-4H-furo[3,2-b]indole-2-carboxylic acid. Recrystallization of the crude product from N,N-dimethylformamide/water yielded 2.3 g (64% yield) of the tetrazole amide in analytical purity as a complex containing 1.0 mole of N,N-dimethylformamide, mp 243°–247° C.

EXAMPLE 20

3-Methoxy-4-methyl-4H-furo[3,2-b]indole-2-carboxamide

A flask fitted with a Dewar condenser containing dry ice/acetone was cooled in a dry ice/acetone bath and charged with 350 ml of anhydrous ammonia. A few crystals of hydrated ferric nitrate catalyst were added, and the cooling bath was removed. Lithium amide was then generated by the addition, over one hour, of 1.78 g (0.26 mole) of freshly cut lithium metal ribbon. After the addition of 65 ml of cold tetrahydrofuran, a solution of 16.5 g (0.060 mole) of 3-methoxy-4-methyl-4H-furo[3,2-b]indole-2-carboxylic acid ethyl ester in 75 ml of tetrahydrofuran was added over 30 minutes. The Dewar condenser was removed, and the mixture was stirred for 16 hours as the excess ammonia evaporated. The total reaction mixture was added to 600 g of ice/water, and the crude amide product was filtered and washed with water. Recrystallization from aqueous ethanol yielded 11.7 g (79% yield) of final product, mp 174°–177° C. An additional recrystallization as above yielded an analytically pure sample, mp 179°–182° C.

EXAMPLE 21

3-Methoxy-4-methyl-4H-furo[3,2-b]indole-2-carbonitrile

A mixture of 11.7 g (0.048 mole) of 3-methoxy-4-methyl-4H-furo[3,2-b]indole-2-carboxamide, 11.7 ml (11.5 g, 0.15 mole) of pyridine, and 14.0 g (0.073 mole) of p-toluenesulfonyl chloride in 70 ml of N,N-dimethylformamide was heated on the steam bath under a nitrogen atmosphere for four hours. The mixture was cooled and added to 500 g ice/water, and the crude nitrile product was filtered and washed with water. Recrystallization from ethanol yielded 9.5 g (88% yield) of the analytically pure nitrile, mp 144°–146° C.

EXAMPLE 22

3-Methoxy-4-methyl-2-(1H-tetrazol-5-yl)-4H-furo-[3,2-b)indole

A mixture of 11.3 g (0.050 mole) of 3-methoxy-4-metyl-4H-furo[3,2-b]indole-2-carboxamide, 10.0 g (0.15 mole) of sodium azide, and 8.5 g (0.16 mole) of ammonium chloride in 225 ml of N,N-dimethylformamide was heated on the steam bath under a nitrogen atmosphere for 90 hours. The mixture was cooled, added to 1500 g ice/water, and maintained at 0°–5° C. while being acidified with 6N hydrochloric acid (hydrazoic acid is evolved). The crude tetrazole product was filtered and washed with water. Recrystallization from 2-methoxyethanol/water yielded 7.5 g (56% yield) of the product. Several additional recrystallizations from acetone/water yielded an analytically pure sample containing 0.25 mole of water of hydration, mp 173° C. (dec).

EXAMPLE 23

3,7-Dimethoxy-4-phenyl-4H-furo[3,2-b]indole-2-carboxamide

Prepared by the procedure described in Example 20 from 19.5 g (0.056 mole) of 3,7-dimethoxy-4-phenyl-4H-furo[3,2-b]indole-2-carboxylic acid methyl ester. Recrystallization of the crude product from aqueous ethanol yielded 13.4 g (72% yield) of amide, mp 210°–212° C. An additional recrystallization as above yielded an analytically pure sample, mp 210°–211° C.

EXAMPLE 24

3,7-Dimethoxy-4-phenyl-4H-furo[3,2-b]indole-2-carbonitrile

Prepared by the procedure described in Example 21 from 12.5 g (0.037 mole) of 3,7-dimethoxy-4-phenyl-4H-furo[3,2-b]indole-2-carboxamide. Recrystallization of the crude product from ethanol yielded 8.6 g (73% yield) of nitrile, mp 137°–139° C. An additional recrystallization as above yielded an analytically pure sample of identical mp.

EXAMPLE 25

3,7-Dimethoxy-4-phenyl-2-(1H-tetrazol-5-yl)-4H-furo[3,2-b]indole

Prepared by the procedure described in Example 22 from 7.2 g (0.023 mole) of 3,7-dimethoxy-4-phenyl-4H-furo[3,2-b]indole-2-carbonitrile, except that the heating time was reduced to 19 hours. The crude tetrazole product after washing with water was recrystallized from 2-methoxyethanol/water and then from acetone/water to yield 3.3 g (40% yield) of product, mp 189°–191° C. An additional recrystallization from acetone/water yielded an analytically pure sample containing 0.5 mole of water of hydration, mp 191°–192° C.

EXAMPLE 26

1,2-Dihydro-6-methoxy-1-phenyl-4H-3,1-benzoxazine-4-one

A mixture of 15.0 g (0.062 mole) of 5-methoxy-2-(phenylamino)benzoic acid and 75 ml of 37% aqueous formaldehyde solution in 75 ml of ethanol was heated on the steam bath for 75 minutes. The mixture was cooled and added to 400 g ice/water. The crude oxazine product was filtered, stirred in 75 ml of 5% aqueous sodium bicarbonate, and refiltered to yield 13.0 g (83% yield) of the product, mp 99.5°–101° C. A sample recrystallized from hexane was analytically pure, mp 100°–102° C.

EXAMPLE 27

2-[(Cyanomethyl)phenylamino]-5-methoxy-benzoic acid

To a solution of 268 g (4.1 mole) of potassium cyanide in 1.6 l of water was added 1021 g (4.0 mole) of 1,2-dihydro-6-methoxy-1-phenyl-4H-3,1-benzoxazine-4-one at a rate such that the reaction mixture temperature was 35°–40° C. The resulting solution was stirred and maintained at 35°–40° C. for two hours, and then added dropwise to a solution of 8.0 l of ice water and 800 ml of acetic acid. The resulting suspended solid was filtered and washed with water to yield 1084 g (96% yield) of the crude nitrile, mp 122°–130° C. This material was used for further synthesis without additional purification.

EXAMPLE 28

2-[(Carboxymethyl)phenylamino]-5-methoxy-benzoic acid

To a solution of 3.4 l of 25% aqueous sodium hydroxide being stirred at reflux was added 1936 g (6.86 mole) of 2-[(cyanomethyl)phenylamino]-5-methoxy-benzoic acid in portions over one hour. After the addition of 1.0 l of water, the resulting solution was stirred at reflux for an additional hour. The solution was cooled, added to 18 kg ice/water, and treated with acetic acid until pH 7. The mixture as filtered, and the filtrate was cooled in ice and made strongly acidic with concentrated hydrochloric acid. The resulting solid was filtered and washed with water to yield 1612 g (78% yield) of the crude diacid product, mp 158°–161° C. This material was converted to the diester without additional purification.

EXAMPLE 29

5-Methoxy-2-[(2-methoxy-2-oxoethyl)phenylamino]-benzoic acid methyl ester

A mixture of 113 g (0.40 mole) of 2-[(carboxymethyl)-phenylamino]-5-methoxy-benzoic acid in 800 ml of N,N-dimethylformamide was treated with 128 g (0.80 mole) of 25% aqueous sodium hydroxide. After stirring at ambient temperature for 30 minutes, there was added 156 g (1.10 mole) of iodomethane. The mixture was stirred without external heating for three hours, then warmed to 50°–55° C. for 30 minutes. The reaction mixture was added to 1 kg ice/water and the product was extracted by washing several times with dichloromethane. The combined organic layers were backwashed with saturated sodium bicarbonate solution, then water, and dried over anhydrous sodium sulfate. Evaporation of the organic layer left the crude diester as an oil, 106 g (80% yield), which was used for additional synthesis. A sample of the oil crystallized from methanol yielded the final product as a solid in analytical purity, mp 85°–87° C.

EXAMPLE 30

3-Hydroxy-5-methoxy-1-phenyl-1H-indole-2-carboxylic acid methyl ester

A mixture of 1.7 kg (5.2 mole) of 5-methoxy-2-[(2-methoxy-2-oxoethyl)phenylamino]benzoic acid methyl ester, and 303 g (5.6 mole) of sodium methoxide in 10.0 l of anhydrous methanol was stirred at reflux for 90 minutes. The mixture was cooled to 20° C., filtered, and treated with 336 g (320 ml, 5.6 mole) of glacial acetic acid. The mixture was cooled in ice, and the precipitated crude product was filtered and washed with cold methanol followed by hexane. There was obtained 1267 g (82% yield) of the indole product of analytical purity, mp 114°–116° C.

EXAMPLE 31

3-Methoxy-4-phenyl-4H-furo[3,2-b]indole-2-carboxamide

Prepared by the procedure described in Example 20 from 23.3 g (0.073 mole) of 3-methoxy-4-phenyl-4H-furo-[3,2-b]indole-2-carboxylic acid methyl ester. Recrystallization of the crude product from absolute ethanol yielded 13.7 g (61% yield) of analytically pure amide containing 0.20 mole of water of hydration, mp 207°–208° C.

EXAMPLE 32

3-Methoxy-4-phenyl-4H-furo[3,2-b]indole-2-carbonitrile

Prepared by the procedure described in Example 21 from 13.4 g (0.044 mole) of 3-methoxy-4-phenyl-4H-furo-[3,2-b]indole-2-carboxamide. Recrystallization of the crude product from ethanol/N,N-dimethylformamide yielded 10.3 g (82% yield) of analytically pure nitrile, mp 182°–184° C.

EXAMPLE 33

3-Methoxy-4-phenyl-2-(1H-tetrazol-5-yl)-4H-furo-[3,2-b]-indole

Prepared by the procedure described in Example 25 from 8.9 g (0.031 mole) of 3-methoxy-4-phenyl-4H-furo-[3,2-b]indole-2-carbonitrile. The crude product was recrystallized from dichloromethane/methanol/hexane to yield 3.0 g (29% yield) of analytically pure tetrazole, mp 212° C. (dec).

EXAMPLE 34

3-Ethoxy-4-phenyl-4H-furo[3,2-b]indole-2-carboxylic acid

A suspension of 12.0 g (0.036 mole) of 3-ethoxy-4-phenyl-4H-furo[3,2-b]indole-2-carboxylic acid methyl ester in 100 ml of methanol was treated with 60 ml of 1.0 N aqueous sodium hydroxide. After stirring at reflux for 20 hours, the cooled reaction mixture was added to 1.2 kg ice/water, and the mixture was acidified with acetic acid. The crude product was filtered, stirred in 600 ml water, and refiltered. Recrystallization from ethanol yielded 5.1 g of analytically pure acid containing 0.35 mole of water of hydration, mp 146°–147° C. An additional 1.8 g of product was obtained from the recrystallization filtrate, for a total yield of 6.9 g (59% yield).

EXAMPLE 35

3-Ethoxy-4-phenyl-N(1H-tetrazol-5-yl)-4H-furo[3,2-b]-indole-2-carboxamide

Prepared by the procedure described in Example 5 from 4.7 g (0.015 mole) of 3-ethoxy-4-phenyl-4H-furo-[3,2-b]indole-2-carboxylic acid. Recrystallization of the crude product from N,N-dimethylformamide yielded 3.4 g (50% yield) of the tetrazole amide in analytical

EXAMPLE 36

3-Ethoxy-4-phenyl-4H-furo[3,2-b]indole-2-carboxamide

Prepared by the procedure described in Example 20 from 8.5 g (0.025 mole) of 3-ethoxy-4-phenyl-4H-furo-[3,2-b]indole-2-carboxylic acid methyl ester. The crude amide product, after being washed with water and dried, was 7.5 g (92% yield). This material was converted to the nitrile without additional purification. A portion of the crude amide recrystallized from ethanol yielded an analytically pure sample, mp 187°–188° C.

EXAMPLE 37

3-Ethoxy-4-phenyl-4H-furo[3,2-b]indole-2-carbonitrile

Prepared by the procedure described in Example 21 from 6.5 g (0.020 mole) of 3-ethoxy-4-phenyl-4H-furo-[3,2-b]indole-2-carboxamide. The crude product (5.5 g, 90% yield), after being washed with water and dried, was converted to the corresponding tetrazole without additional purification. A portion of the crude nitrile recrystallized from methanol yielded an analytically pure sample, mp 121°–122° C.

EXAMPLE 38

3-Ethoxy-4-phenyl-2(1H-tetrazol-5-yl)-4H-furo-[3,2-b]indole

Prepared by the procedure described in Example 22 from 5.3 g (0.018 mole) of 3-ethoxy-4-phenyl-4H-furo-[3,2-b]indole-2-carbonitrile. The crude product was chromatographed over silica gel to remove unreacted nitrile. A sample recrystallized from ethanol was analytically pure, mp 189°–192° C.

EXAMPLE 39

3,7-Dimethoxy-4-phenyl-4H-furo[3,2-b]indole-2-carboxylic acid, tris(hydroxymethyl)aminomethane salt A suspension of 0.67 (0.0020 mole) of 3,7-dimethoxy-4-phenyl-4H-furo[3,2-b]indole-2-carboxylic acid in 100 ml of warm methanol was treated with a warm solution of 0.25 g (0.0021 mole) of tris(hydroxymethyl)aminomethane in 30 ml of methanol. The mixture was digested on the steam bath until nearly one phase, then was filtered hot. The cooled filtrate was evaporated, and the residue was recrystallized from methanol/ether to yield 0.50 g (53% yield) of the hygroscopic "TRIS" salt, mp 151°–153° C.

EXAMPLE 40

3,7-Dimethoxy-4-phenyl-N-(1H-tetrazol-5-yl)-4H-furo-[3,2-b]indole-2-carboxamide, sodium salt A suspension of 11.0 g (0.027 mole) of 3,7-dimethoxy-4-phenyl-N-(1H-tetrazol-5-yl)-4H-furo-[3,2-b]indole-2-carboxamide in 300 ml of warm methanol was treated with a warm solution of 28.0 ml (0.028 mole) of 1.0 N aqueous sodium hydroxide. The mixture was digested on the steam bath and then filtered hot. Cooling yielded a precipitate, which was filtered and washed several times with cold acetone. There was obtained 5.2 g (45% yield) of the carboxamido tetrazole sodium salt, mp 268° C. (dec).

EXAMPLE 41

3,7-Dimethoxy-4-phenyl-N-(1H-tetrazol-5-yl)-4H-furo-[3,2-b]indole-2-carboxamide, L-(+)-arginine salt Prepared by the procedure described in Example 40 from 11.0 g (0.027 mole) of 3,7-dimethoxy-4-phenyl-N-(1H-tetrazol-5-yl)-4H-furo[3,2-b]indole-2-carboxamide in 500 ml of methanol and a solution of 5.1 g (0.029 mole) of L-(+)-arginine in 15 ml of warm water. There was obtained 6.8 g (42% yield) of the hygroscopic arginine salt, mp 170° C. (dec).

EXAMPLE 42

3-Ethoxy-7-methoxy-4-phenyl-N-(1H-tetrazol-5-yl)-4H-furo[3,2-b]indole-2-carboxamide, L-(+)-arginine salt Prepared by the procedure described in Example 39 from 3.0 g (0.0072 mole) of 3-ethoxy-7-methoxy-4-phenyl-N-(1H-tetrazol-5-yl)-4H-furo[3,2-b]indole-2-carboxamide in 350 ml of methanol and a solution of 1.4 g (0.0080 mole) of L-(+)-arginine in 3.0 ml of water. Recrystallization of a sample of the residue from methanol/acetone yielded the hygroscopic arginine salt, mp 155° C. (dec).

EXAMPLE 43

3,7-Dimethoxy-4-phenyl-N-(1H-tetrazol-5-yl)-4H-furo-[3,2-b]indole-2-carboxamide, piperidine salt Prepared by the procedure described in Example 39 from 2.54 g (0.0063 mole) of 3,7-dimethoxy-4-phenyl-N-(1H-tetrazol-5-yl)-4H-furo[3,2-b]indole-2-carboxamide in 200 ml of methanol and 3.0 ml (2.58 g; 0.030 mole) of added piperidine. Recrystallization of the residue from methanol/acetone yielded 1.75 g (55% yield) of the hygroscopic piperidine salt, mp 161°–164° C.

EXAMPLE 44

3,7-Dimethoxy-4-phenyl-N-(1H-tetrazol-5-yl)-4H-furo-[3,2-b]indole-2-carboxamide, hemi-1,2-ethanediamine salt Prepared by the procedure described in Example 39 from 3.0 g (0.0074 mole) of 3,7-dimethoxy-4-phenyl-N-(1H-tetrazol-5-yl)-4H-furo[3,2-b]indole-2-carboxamide in 200 ml of methanol and 0.6 ml (0.54 g; 0.0090 mole) of added 1,2-ethanediamine. Recrystallization of the residue from methanol/ether yielded 1.8 g (56% yield) of the hygroscopic hemi-1,2-ethanediamine salt, mp 150° C. (dec).

I claim:

1. A compound having the structural formula I

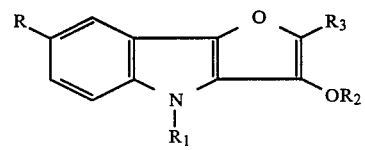

wherein R is H, alkyl of from one to six carbon atoms, alkoxy of from one to six carbon atoms, halogen or nitro; $R_1$ is phenyl; $R_2$ is alkyl of from one to six carbon atoms; $R_3$ is

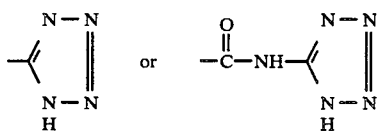

and the pharmaceutically acceptable salts thereof.

2. The compound defined in claim 1 having the name 3,7-dimethoxy-4-phenyl-N-(1H-tetrazol-5-yl)-4H-furo[3,2-b]indole-2-carboxamide, and the pharmaceutically acceptable salts thereof.

3. The sodium salt of the compound of claim 2.

4. The L-(+) arginine salt of the compound of claim 2.

5. The compound defined in claim 1 having the name 3-ethoxy-4-phenyl-N-(1H-tetrazol-5-yl)-4H-furo[3,2-b]indole-2-carboxamide, and the pharmaceutically acceptable salts thereof.

6. The compound defined in claim 1 having the name 3-methoxy-4-phenyl-2-(1H-tetrazol-5-yl)-4H-furo[3,2-b]indole, and the pharmaceutically acceptable salts thereof.

7. The compound defined in claim 1 having the name 3-ethoxy-4-phenyl-2-(1H-tetrazol-5-yl)-4H-furo[3,2-b]indole, and the pharmaceutically acceptable salts thereof.

8. The compound defined in claim 1 having the name 3-methoxy-4-phenyl-N-(1H-tetrazol-5-yl)-4H-furo[3,2-b]indole-2-carboxamide, and the pharmaceutically acceptable salts thereof.

9. The compound defined in claim 1 having the name 3-ethoxy-7-methoxy-4-phenyl-N-(1H-tetrazol-5-yl)-4H-furo[3,2-b]indole-2-carboxamide, and the pharmaceutically acceptable salts thereof.

10. The L-(+) arginine salt of the compound of claim 12.

11. The compound defined in claim 1 having the name 3,7-dimethoxy-4-phenyl-2-(1H-tetrazol-5-yl)-4H-furo[3,2-b]indole, and the pharmaceutically acceptable salts thereof.

12. A pharmaceutical composition comprising an anti-allergically effective amount of a compound as defined in claim 1 in combination with a pharmaceutically acceptable carrier.

13. A method for treating allergies in a mammal in need of such treatment which comprises administering an effective amount of the pharmaceutical composition defined in claim 12 to said mammal.

* * * * *